(12) United States Patent
Wang et al.

(10) Patent No.: US 6,867,194 B2
(45) Date of Patent: Mar. 15, 2005

(54) ENZYME ACTIVATED NITRIC OXIDE DONORS

(75) Inventors: Peng George Wang, Troy, MI (US); Xuejun Wu, Detroit, MI (US); Xiaoping Tang, Lansdale, PA (US)

(73) Assignee: Wayne State University, Detroit, MI (US)

( * ) Notice: Subject to any disclaimer, the term of this patent is extended or adjusted under 35 U.S.C. 154(b) by 376 days.

(21) Appl. No.: 09/925,816

(22) Filed: Aug. 9, 2001

(65) Prior Publication Data

US 2003/0050256 A1 Mar. 13, 2003

(51) Int. Cl.[7] ............................................. A61K 3/785
(52) U.S. Cl. ..................... 514/26; 536/17.5; 536/118; 536/119; 536/124; 536/17.3; 536/18.7; 536/20; 536/23.1; 435/97; 435/193; 510/392; 510/310; 526/238.2
(58) Field of Search ..................... 514/26; 536/17.5, 536/118, 119, 124, 17.3, 18.7, 20, 23.1; 435/97, 193; 510/392, 310; 526/238.2

(56) References Cited

U.S. PATENT DOCUMENTS

| | | |
|---|---|---|
| 4,845,091 A | 7/1989 | Schonafinger et al. |
| 5,910,316 A | 6/1999 | Keefer et al. |
| 5,958,427 A | 9/1999 | Salzman |
| 6,013,635 A | 1/2000 | Heerze et al. |
| 6,140,041 A * | 10/2000 | LaClair ........................... 435/4 |
| 6,290,981 B1 * | 9/2001 | Keefer et al. ................ 424/423 |

OTHER PUBLICATIONS

Xuejun Wu, et al, "Glycosylated diazenlumdiolates: a novel class of enzyme activated nitric oxide donors," Tetrahedron Letters 2001, 42, 3779–3782.

Carlos A. Valdez, et al., "Carbohydrates as Novel Diazeniumdiolate Protecting Groups," American Chemical Society Meeting at Chicago, Jul. 20, 2001. Abstract # 43. Division of Carbohydrate Chemistry.

Christian G. Stief, et al., "Preliminary Results With Nitric Oxide Donor Linsidomine Chlorhydrate in the Treatment of Human Erectile Dysfunction," The Journal of Urology, vol. 148, 1437–1440, Nov. 1992.

Hartmut E. H, Wegner, M.D., et al., "Effect of Nitric Oxide–Donor, Linsidomine Chlorhydrate, in Treatment of Human Erectile Dysfunction Caused by Venous Leakage," Urology, vol. 42, No. 4, Oct. 1993.

Saavedra, Joseph, et al., "Esterase–Sensitive Nitric Oxide Donors of the Diazeniumdiolate Family: In Vitro Antileukemic Activity,"J. Med. Chem. 2000, 43, 261–269.

Tang, Xiaoping, "Synthesis of Peptide–Diazeniumdiolate Conjugates: Towards Enzyme Activated Antitumor Agents, "Tetrahedron Letters 42 (2001) 2625–2629.

* cited by examiner

Primary Examiner—James O. Wilson
Assistant Examiner—Devesh Khare
(74) Attorney, Agent, or Firm—Brinks Hofer Gilson & Lione

(57) ABSTRACT

Sugar-modified SIN-1 compositions are provided. The compositions are useful for generating NO in response to hydrolytic activity of a glycosidase specific for the O-glycosidic bond between the sugar and SIN-1 moieties. Pharmaceutical compositions containing the sugar-modified SIN-1 compositions and methods of using the compositions are also provided.

20 Claims, 1 Drawing Sheet

Generation of ONOO⁻ from β-Gal-SIN-1

Generation of ONOO⁻ from β-Gal-SIN-1

ENZYME ACTIVATED NITRIC OXIDE DONORS

FEDERALLY SPONSORED RESEARCH OR DEVELOPMENT

Figure 1:
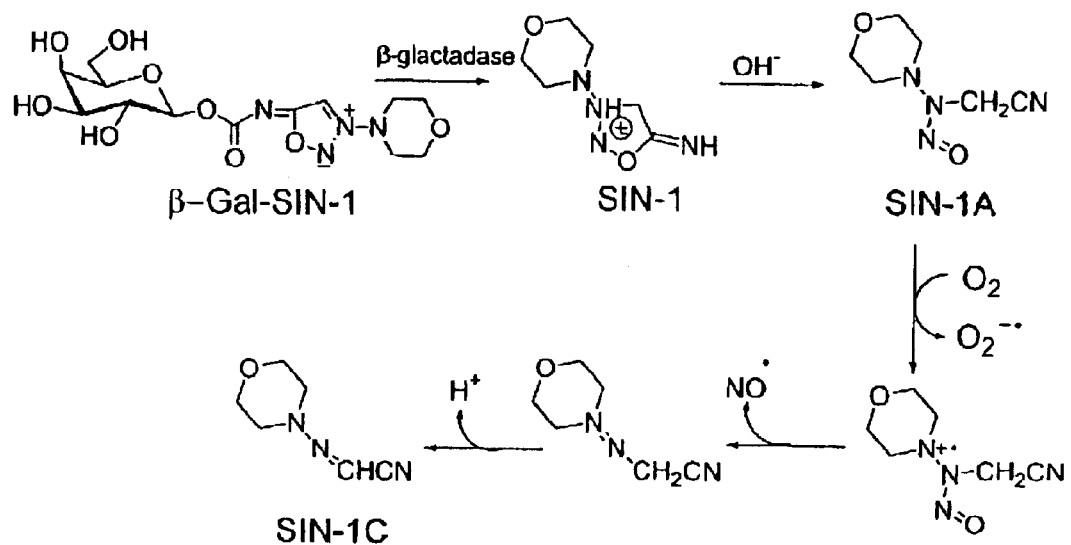
Figure 1:

The U.S. Government may have rights in the present invention pursuant to the terms of grant number GM54074-07 awarded by the National Institute of Health.

FIELD OF THE INVENTION

The invention relates to nitric oxide donor compounds. More particularly, the invention relates to compounds that deliver nitric oxide following activation by a glycosidase. Furthermore, the invention relates to pharmaceutical compositions that include the glycosidase activated nitric oxide donors and to methods of using these compounds.

The compounds, by their ability to release nitric oxide, are useful for regulating many physiological processes, such as vasodilation and generation of tumoricidal activity.

BACKGROUND OF THE INVENTION

Nitric Oxide (NO) plays a variety of roles in a number of physiological processes. In fact NO can be viewed as a double-edged sword in terms of its biological functions. On one hand, NO exerts beneficial regulatory effects in a variety of tissues. For example, NO has well-characterized vasoactive properties (see, for example, Martin, J.; Angeles, M. R.-M. *Pharmocol. Ther.* 1997, 75, 111; Pfeiffer, S.; Mayer, B.; Hemmens, B. *Agnew. Chem., Int. Ed.* 1999, 38, 1714; Furchgott, R. F. *Agnew. Chem. Int.* 1999, 38, 1870). Also, the role of NO as a neurotransmitter has been thoroughly explored (see, for example, Hibbs, J. B.; Taintor, R. R.; Varvin, Z. Science 1987, 235, 473; Nathan, C.; Hibbs, J. B. *Curr. Opin. Immunol.* 1991, 3, 65). In addition, NO plays a role in host defense systems. For example, nitric oxide is generated in response to a variety of stimuli (see, Hibbs, J. B., Westenfelder C., Taintor R. et al., *J. Clin Invest* 1992, 89, 867; Bukrinsky M.; Schmidtmayerova H.; Zybarth G.; Dubrovsky L., Sherry B.; Enikolopov G., *Mol Med* 1996, 2, 460; Zambala M.; Siedlar M.; Marcinkiewicz J.; Pryjma J. *Eur J Immunol* 1994, 24, 435), including bacteria and cytokines (see, Denis M.; *J Leukoe Biol* 1991, 49, 380). Furthermore, macrophages, kupffer cells, natural killer cells, and endothelial cells participate in tumoricidial activity, at least in part, by producing NO (Garthwaite, J.; Charles, S. L.; Chess-Williams, R., *Nature* 1988, 336, 385; Gillespi, J. S.; Liu, X.; Martin, W., Br. *J. Pharmacol.* 1989, 98, 1080).

NO can be easily converted into a variety of reactive nitrogen species (RNS), such as $N_2O_3$, $NO_2$ and $ONOO^-$ (peroxynitrite anion). While these RNS are highly reactive, their reactivity can be utilized to achieve beneficial results. For example, peroxynitrite anion is a potent oxidizing and nitrating species capable of inducing molecular damage in DNA, such as strand breaks. Sufficient generation of this RNS can lead to cellular dysfunction, up to and including cytotoxicity (see Koppenol, W. H., *Free Radic, Biol. Med*, 1998, 25, 385–391; Murphy, M. P.; Packer, M. A.; Scarlett, J. L. ; Martin, S. W., *Gen. Pharmacol.* 1998, 31, 179–186; Douki, T.; Cadet, J.; Ames, B. N., *Chem Res. Toxicol.* 1996, 9, 3–7). By controlling the generation of this RNS to a localized area in which it is desirable to kill cells, such as in a solid tumor, the reactivity of peroxynitrite anion can be used to achieve a desired result.

As a result, targeted or specific delivery of NO to a site of interest could provide a useful mechanism to harness the reactivity of various RNS. Although delivering NO in its gaseous form may have some benefits (see, Nelin L; Moshin C; Sasidharan T; Dawson C, Pediatric Research 1994, 35, 20 Etches P; Finer K; Barrington A; Graham A; Chan W, Pediatric Research 1994, 35, 15), NO gas is highly reactive itself in a generally nonspecific manner. To utilize the cytotoxic effects of NO in a selective manner, NO must be delivered to the targeted cells or sites while minimizing exposure to those not targeted.

SUMMARY OF THE INVENTION

The present invention provides a class of NO donor compounds, pharmaceutical compositions that include the donor compounds, and methods of using the donor compounds to deliver NO to a targeted cell by taking advantage of the role of carbohydrates in cell recognition and internalization processes. The donor compounds include a carbohydrate moiety and release NO through the hydrolytic action of glycosidase enzymes. Such site specific delivery will facilitate various treatments that can benefit from the properties of NO, such as cytotoxicity treatment of solid tumors.

The NO donor compounds according to the present invention are sugar-modified linsidomines, also known as 3-morpholinosydnonimine and commonly referred to as SIN-1. In these compositions, a sugar moiety is linked to SIN-1 via a glycosidic bond. Preferably, a linker group, such as a carbonyl group, is disposed between the sugar and SIN-1 moieties.

As a NO donor, SIN-1 is attractive because it is believed to generate NO nonenzymatically (see Steif, C.; Holmquist, F.; Djamilian M.; Krah, H.; Andersson, K.; Jonas, U. *The Journal of Urology*, 1992, 148, 1437–1440). The use of SIN-1 as a NO donor for vasoactive applications has been reported (see, for example, Id.) Also, for cytotoxic applications, SIN-1 is attractive because its activation produces both NO and superoxide ion, which combine to produce highly reactive peroxynitrite anion. These reactive species can be used to damage biomolecules, and to induce cytotoxicity. The sugar moiety ensures that the NO donor compound is inactive until it encounters an appropriate activating enzyme, such as a glycosidase. Furthermore, the sugar moiety facilitates the delivery of the NO donor compound, and, consequently, the delivery of the reactive species, by providing selective access to the cell membrane via surface carbohydrates. Accordingly, the NO donor compounds of the present invention can be designed and synthesized to contain a sugar moiety that targets a specific receptor or surface ligand of a particular tissue and/or cell.

The NO donor compounds of the present invention have the following general structure:

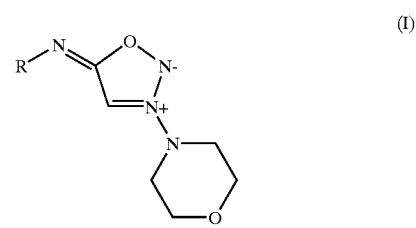

wherein R is any carbohydrate. R can be a monosaccharide, a disaccharide, or a polysaccharide. Furthermore, in the case of disaccharide and polysaccharides, each O-glycosidic bond between sugar units can be in either the α or β configuration.

R can be linked to the SIN-1 moiety via an O-glycosidic bond or a linker group. When present, the O-glycosidic bond between the carbohydrate moiety and the SIN-1 moiety can be in either the α or β configuration.

Preferably, the NO donor compounds also include a linker group disposed between the sugar and SIN-1 moieties. Particularly preferable, the linker group comprises a carbonyl-containing group. Compositions according to this preferred embodiment have the following general structure:

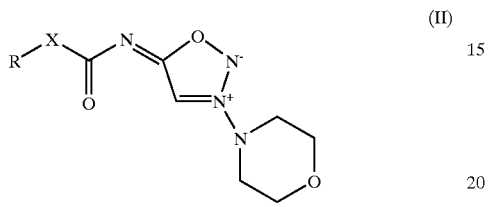

(II)

wherein X is C, N, S, or O. Preferably, X is O.

In preferred NO donor compounds, R is a member selected from the group consisting of β-glucose, β-galactose, α-glucose, and α-galactose. Accordingly, preferred NO donor compounds include the following;

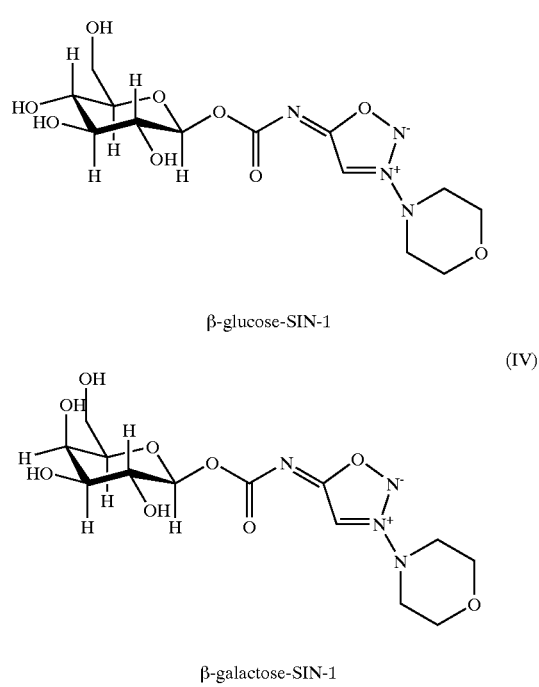

β-glucose-SIN-1 (III)

β-galactose-SIN-1 (IV)

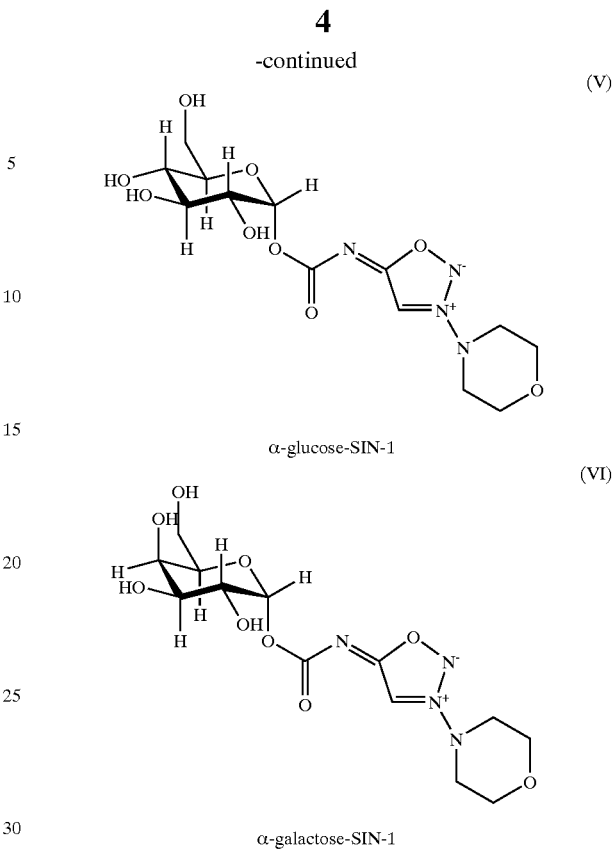

α-glucose-SIN-1 (V)

α-galactose-SIN-1 (VI)

BRIEF DESCRIPTION OF THE FIGS.

FIG. 1 is a scheme of the chemical reactions that generate NO, $O_2^-$, and $ONOO^-$ from β-galactose-SIN-1.

DETAILED DESCRIPTION OF THE PREFERRED EMBODIMENTS OF THE INVENTION

The following description of various preferred embodiments of the invention provides examples of the present invention. The embodiments discussed herein are merely exemplary in nature, and are not intended to limit the scope of the invention in any manner. Rather, the description of these preferred embodiments serves to enable a person or ordinary skill in the relevant art to make, use and practice the present invention.

The invention is directed at a class of NO donor compounds, pharmaceutical compositions containing these compounds, and methods of using the compounds.

General Structure of NO Donors According to the Present Invention

The NO donor compounds according to the present invention have the following general structure:

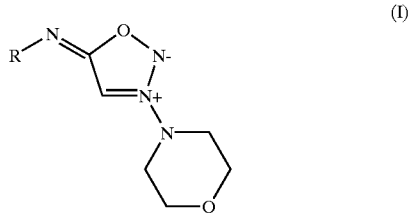

(I)

Preferably, the NO donor compound includes a linker group disposed between the sugar and SIN-1 moieties. Suitable linker groups comprise a bifunctional group that bonds to the SIN-1 moiety at one end and to the sugar moiety at another end. Any suitable linker group known to those skilled in the art can be utilized. Examples of suitable linker groups include those discussed in U.S. Pat. No. 6,013,635 to Heerze, et al., for TREATMENT OF C. DIFFICILE TOXIN B ASSOCIATED CONDITIONS, and U.S. Pat. No. 6,140,041 to LaClair for a FLUORESCENT DYE. Preferred, linker groups comprise carbonyl-containing groups. NO donor compounds in accordance with this preferred embodiment have the following general structure:

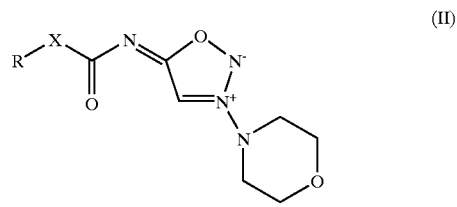

(II)

wherein X is C, N, S, or O. Preferably X is O.

In both structures I and II, R comprises the sugar moiety and can be any carbohydrate. R can be a monosaccharide, a disaccharide, or a polysaccharide. In preferred forms R is a monosaccharide. Any suitable monosaccharide can be used. Suitable monosaccharides include both D- and L-forms of glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, and tagatose. Particularly preferred are monosaccharides in a pyranose or furanose ring formation, such as glucopyranose, galactopyranose, fructofuranose and ribofuranose.

Any suitable disaccharide can be used. Examples of suitable disaccharides include sucrose, lactose and maltose.

Also, the O-glycosidic bond between the carbohydrate moiety and the SIN-1 moiety can be in either the α or β configuration. Furthermore, in the case of disaccharides and polysaccharides, each O-glycosidic bond between sugar units can be in either the α or the β configuration.

In preferred forms, the NO donor compound is β-glucose-SIN-1, β-galactose-SIN-1, α-glucose-SIN-1, or α-galactose-SIN-1, in which R is β-glucose, β-galactose, α-glucose, and α-galactose, respectively. Particularly preferred compositions in accordance with the present invention are N-(β-D-glucopyranosyl)-carbonyl-3-morpholinosydnonimine, N-(α-glucopyranosyl)-carbonyl-3-morpholinosydnonimine, N-(β-D-galactopyranosyl)-carbonyl-3-morpholinosydnonimine, and N-(α-D-galactopyranosyl)-carbonyl-3-morpholinosydnonimine, in which R is either glucopyranosyl or galactopyranosyl.

Synthesis of NO Donors According to the Present Invention

The NO donor compounds according to the present invention can be synthesized according to the generic protocol listed below as Example 1.

Pharmaceutical Compositions Including NO Donors According to the Present Invention The NO donor compounds according to the present invention can be used in pharmaceutical compositions. The pharmaceutical compositions of the present invention are compositions for generating NO upon activation by an appropriate enzyme, such as a glycosidase able to recognize and hydrolyze the glycosidic bond between the sugar and SIN-1 moieties or between the sugar moiety and the linker. The pharmaceutical compositions can also serve as compositions for generating $O_2^-$ and $ONOO^-$ radicals upon activation by an appropriate enzyme.

In preferred forms the pharmaceutical compositions according to the present invention include a therapeutically effective amount of a NO donor compound according to the present invention and a carrier. As used herein, the term "carrier" refers to any composition with which the NO donor can be combined without eliminating its ability to generate NO. Carriers can include, but are not limited to, solvents and additives. A single NO donor compound can be used or a combination of two or more NO donor compounds can be utilized in the pharmaceutical composition. The NO donor compound(s) included in the pharmaceutical composition preferably contain sugar moieties that confer an ability to bind sugar acceptors or other surface ligands on a desired cell surface as an initial step of internalization of the NO donor. Particularly preferable, the sugar moiety of the NO donor compound is able to bind to cells in a tissue that is the target of the subject therapy. This specific targeting of tissues and cells via sugars has been reported and is well characterized (see, for example, Blondin, C.; Bataille, I.; Letourneur, D. *Crit. Rev. Ther. Drug Carrier Syst.* 2000, 17(4), 327; Paillard, F. *Hum. Gene Ther* 1999, 10(3), 337).

The effective dose of the NO donor compound in the pharmaceutical composition will depend on, among other factors, the desired levels of NO and/or superoxide ion and peroxynitrite anion, and the type and quantity of tissue being treated. For a particular application, the effective amount of the NO donor compound should be optimized based on these factors.

Any pharmaceutically acceptable carrier can be used. The carrier may be either a solid or a liquid, and the choice between these alternatives will depend on the application. For example, if the NO donor compound will ultimately be delivered by injection, or other similar drug delivery technique, a liquid vehicle is more appropriate. For compositions having a liquid vehicle, the vehicle preferably comprises saline. Alternatively, other liquid vehicles may be used, either alone or in combination. Suitable vehicles include water, Ringers-Lactate, dimethyl sulfoxide (DMSO), ethanol, other alcohols, glycerol, polyols, vegetable oils, a colloid solution, a crystalloid solution, dextrose, albumin, a surfactant, and the like.

Alternatively, a solid carrier, or a relatively viscous liquid carrier, may be desirable when the NO donor compound will ultimately be delivered by pill or other similar composition. For these compositions the carriers may comprise pharmaceutically inert inorganic excipients in the form of pills, tablets, lacquered tablets, coated tablets, hard and soft gelatin capsules, solutions, syrups, emulsions or suspensions. Also, other forms can be prepared if non-oral or non-inhalation delivery methods are desired. For example, suppositories can be prepared for rectal delivery and ointments, gels, and pastes for topical and percutaneous delivery. To prepare pills, tablets, and capsules, suitable excipients include lactose, maize starch or derivatives thereof, talc, stearic acid, or salts thereof, and the like. Suitable excipients for soft gelatin capsules and suppositories for solutions and syrups include water, sucrose, glucose, polyols, mixtures of these and the like.

Furthermore, the pharmaceutical compositions of the present invention may also contain additives, such as fillers, extenders, disintegrating agents, binders, lubricants, wetting agents, stabilizers, emulsifiers, preservatives, sweeteners, cooling agents, flavoring agents, aromatizing agents, thickeners or diluents, buffer substances, solvents or solubulizing agents, salts, coating agents, and antioxidants.

The NO donor compounds and pharmaceutical compositions according to the present invention can be used in any situation in which it is desirable to generate NO and where an appropriate enzyme is available. The compounds and compositions are particularly well suited for situations in which it is desirable to generate peroxynitrite anion. Furthermore, the compounds and compositions are well suited for situations in which it is desirable to generate NO and/or peroxynitrite anion within a cell that contains carbohydrate acceptors on its cell membrane. Also the compounds and compositions are well suited for situations in which it is desirable to induce damage to biomolecules within such a cell, as well as in situations in which it is desirable to kill such a cell.

Methods of Using the NO Donors According to the Present Invention

Methods of using the NO donor compounds and pharmaceutical compositions of the present invention will now be described. A first preferred method according to the present invention comprises a method of generating NO. A first step of this preferred method comprises providing a NO donor according to the present invention. A second step comprises contacting the NO donor compound with an appropriate enzyme. Essentially any enzyme capable of breaking the glycosidic bond between the carbohydrate moiety and SIN-1 moiety can be utilized. For example, a glycosidase can be used. The specific glycosidase used will depend on the sugar moiety included in the NO donor. The enzyme should be specific for the carbohydrate moiety. Of course, if a pharmaceutical composition includes a mixture of NO donors, an appropriate mixture of enzymes should likewise be utilized.

This step can be conducted within a cell, or exterior to a cell. If it is done in a cell, a bacterial of mammalian cell can be utilized. The sugar-modified SIN-1 must be internalized into the interior of the cell. Preferably, this is accomplished by contacting the sugar-modified SIN-1 with an appropriate carbohydrate moiety on the exterior surface of the cell and allowing the cell to internalize the sugar-modified SIN-1 by natural processes, such as those involving involution of the cell membrane.

Essentially any glycosidase may be used in the method of the present invention. A great number glycosidases are known, and an extensive list of these enzymes and discussion of their chemistry can be reviewed by consulting any of several references, including Bergmeyer, H.; Bergmeyer, J.; Grassi, M., Methods of Enzymatic Analysis, Weinheim, Deerfield Beach, Fla.; c1983 3 ed.; Levvy, G.; Conchie, J., Mammalian glycosidases and their inhibition by aldonolactones, *Methods Enzymol.* 1966, 8, 571–84; Rye, C.; Withers, S., Glycosidase mechanisms, *Curr. Opin. Chem. Biol.* 2000 4(5), 573–580; Yamamoto, K.; Li, S.; Li, Y. Microbial glycosidases, *Carbohydr. Chem. Biol.* 2000, 3, 497–511; Zechel, D.; Withers, S. Glycosidase Mechanism: Anatomoy of a Finely Tuned Catalyst *Acc. Chem. Res.* 2000 33(1), 11–18; Withers, S. Understanding and exploiting glycosidases, *Can. J. Chem.* 1999, 77(1), 1–11; Henrissat, B. Glycosidase families. *Biochem, Soc. Trans.* 1998 26(2), 153–156. Preferred glycosidases include mammalian α-glucosidases, β-glucosidases, α-galactosidases and β-galactosidases. Of course, any suitable glycosidase with specificity for the glycosidic bond present in the sugar-modified SIN-1 NO donor or donors can be utilized.

For each enzyme used, suitable concentrations of enzyme can be determined based on a variety of parameters including desired quantity of reaction product(s). Likewise, if natural enzymes within a cell are employed, suitable concentrations of the NO donor compound can be determined based on expected or actual concentrations of the enzymes present in the cell(s). The cell can be mammalian or bacterial, and those of any kind of pathogenic microorganisms.

Once the NO donor compound contacts the appropriate enzyme, a series of chemical reactions occur to release NO from the SIN-1 moiety and generate other RNS. FIG. 1 provides a schematic representation of the release of NO and subsequent generation of peroxynitrite anion from β-galactose-SIN-1. First, NO is released from the SIN-1 moiety of the NO donor compound. Next, once NO is released, a series of reactions occur to produce peryoxynitrite anion. While not intending to be bound by any particular theory, it is believed that SIN-1 generates NO, and ultimately peroxynitrite anion, in an enzyme independent manner. This process is believed to proceed as follows: SIN-1 reacts with hydroxide ion (OH$^-$) to give SIN-1A. SIN-1A reacts with $O_2$ to form superoxide ion ($O_2^-$) and charged SIN-1A. The charged SIN-1A gives off NO, and eventually a hydrogen ion (H$^+$) to form SIN-1C. The generated NO and superoxide ion can be contacted to react to form peroxynitrite anion (ONOO$^-$). As indicated above, NO, $O_2^-$, and ONOO$^-$ are all highly reactive species capable of damaging biomolecules and even inducing cytotoxicity. Peroxynitrite anion is highly toxic, and is therefore more efficient in inducing such damage and cytotoxicity.

A method of the present invention may further comprise contacting a NO donor according to the present invention with a cell. In this method, the cell preferably contains one or more carbohydrate acceptors on its cell membrane, and the NO donor compound preferably contains a carbohydrate moiety suitable for allowing the NO donor compound to bind to the carbohydrate acceptor on the cell membrane. Preferably, this binding occurs in a biochemically specific manner. Eventually, the NO donor compound is preferably internalized by the cell. Following internalization, contacting the NO donor compound with appropriate enzymes within the cell can occur, thereby activating the SIN-1 moiety. The NO donor compound is preferably delivered to the cell in a selective manner. Methods of selectively delivering compounds to cells are known in the art.

Considering the cytotoxic effects of NO and the other RNS that can be generated via the NO donor compounds of the present invention, in conjunction with the ability to use the carbohydrate moiety to target the NO donor compound to a specific tissue, cell, or cell-type, the present invention also provides a method of selectively destroying a cell. Preferably, this method comprises contacting a therapeutically effective amount of a sugar-modified SIN-1 with the cell and contacting the sugar-modified SIN-1 with an appropriate glycosidase. Once the glycosidase contacts the sugar-modified SIN-1, the NO and the other RNS can be released.

The method may further comprise internalizing the sugar-modified SIN-1 into the interior of the cell, which can proceed following binding between the sugar moiety and a ligand on the surface of the cell. Preferably, the sugar-modified SIN-1 contains a sugar-moiety that is able to bind to the cell. Particularly preferable, the sugar moiety is able to selectively bind to the cell.

In this method, the therapeutically effective amount of the sugar-modified SIN-1 comprises an amount that is sufficient to generate the desired cytotoxic effects. If cytotoxicity is to be limited to a particular group of cells, tissue, section of tissue, or to another restricted location, the amount of sugar-modified SIN-1 can be optimized based on the ability of NO and the other RNS to kill the cell types involved.

This method is particularly well-suited for killing cancerous cells, such as those in solid tumors like tumors located in muscle, neural, ocular, colon, prostate, breast, lung, skin, liver, bone, pancreas, ovary, testis, bladder, kidney, or brain tissue.

EXAMPLES

Example 1

Generic Protocol for Synthesis of NO Donor Components According to the Present Invention.

The Preparation of SIN-1 Acceptors

All glycoses with unprotected anomeric hydroxyl group were obtained by treating peracetylated glycose with $BnNH_2$ in THF at ambient temperature (Sim, M. M.; Kondo, H.; Wong, C.-H. *J. Am. Chem. Soc.* 1993, 115, 2260–2267). $BnNH_2$ was removed by washing the crude product dissolved in $CH_2Cl_2$ with diluted aqueous HCl solution. The product can be further purified by chromatography, then it was coupled with 1.2 equivalents of 4-nitrophenyl chloroformate in the presence of 3 equivalents of triethylamine in anhydrous $CH_2Cl_2$ at 0° C., providing the SIN-1 acceptor, 4-nitrophenyl (peracetyl-($\alpha/\beta$-D-glycosyl) carbonate (Azoulay, M.; Florent, J.-C.; Monneret, C.; Gesson, J. P.; Jacquesy, J.-C.; Tillequin, F.; Koch, M.; Bosslet, K.; Czech, J.; Hoffman, D. *Anti-Cancer Drug Design* 1995, 10, 441–450).

The Preparation of SIN-1

The SIN-1 moieties can be synthesized following Masuda's procedure (Masuda, K.; Imashiro, Y.; Kaneko, T. *Chem. Pharm. Bull.* 1970, 18, 128–132). An aqueous solution of 4-aminomorpholine and formaldehyde-sodium bisulfite (1 eq) was stirred for several hours at room temperature, then KCN (1 eq) was added, and the reaction mixture was heated to about 60° C. and kept stirring for another several hours. Then the reaction mixture was extracted with EtOAc and washed with brine, and the extract was dried over anhydrous $Na_2SO_4$. After removing the solvent, the crude product was directly nitrosated with aqueous sodium nitrite (1.2 eq) solution in the presence of HCl with ice-cooling. The resulting mixture was extracted with EtOAc. The combined organic solution was dried over anhydrous $Na_2SO_4$, then concentrated to give a oily residue, to which was added an excess amount of methanolic hydrochloric acid. The mixture was stirred for several hours and concentrated to afford an off-white solid, which was collected by filtration and washed with ether. The compound can be further purified by recrystallization from ethyl alcohol. SIN-1 was obtained in the form of hydrochloride salt.

The Synthesis of Glycosyl-carbonyl-SIN-1

The coupling reaction of SIN-1 with protected glycosyl carbonate was carried out at room temperature pyridine. The reaction mixture was stirred overnight and then the solvent was removed in vacuo. The crude product was purified by silica gel column chromatography and usually $\alpha$ and $\beta$ forms of products could be separated. The acetyl protecting groups were removed in anhydrous methyl alcohol in the presence of catalytic amount of $NaOCH_3$. This deprotection step required several hours in room temperature. The pure target compounds could be obtained after silica gel chromatography.

Example 2

Synthesis of N-($\beta$D-glucopyranosyl)-carbonyl-3-morpholinosydnonimine

In this example, N-($\beta$-D-glucopyranosyl)-carbonyl-3-morpholinsodnonimine, a sugar-modified SIN-1 according to the present invention, is synthesized from a starting material of D-glucose-pentacetate. Intermediates in this synthesis include 2,3,4,6-tetra-O-acetyl-$\alpha/\beta$-D-glucopyranose, 4-nitrophenyl (2,3, 4,6-tetra-O-acetyl-$\alpha/\beta$-D-glucopyranosyl) carbonate, and N-(2,3,4,6-tetra-O-acetyl-$\alpha/\beta$-D-glucopyranosyl)-carbonyl-3-morpholinosyndonimine. This protocol yields both the $\alpha$ and $\beta$ forms of the sugar-modified SIN-1.

2,3,4,6-Tetra-O-$\alpha/\beta$-D-glucopyranose

A solution of pentaacetate-D-glucose (3.9 g, 10.0 mmol) and $BnNH_2$ (1.2 mL, 11.0 mmol) in THF (45 mL) was stirred at ambient temperature for 30 hours. The solvent was removed and the residue was dissolved in $CH_2Cl_2$ (100 mL), then washed with 1 N HCl (100 mL×2), water (100 mL) successively. The organic layer was concentrated and chromatographed on silica gel with EtOAc/hexane (2/1~1/1), giving 2,3,4,6-tetra-O-$\alpha/\beta$-D-glucopyranose (3.2 g, 9.2 mmol, yield 92%) as a 3:1 ($\alpha/\beta$) mixture of anomers as judged by $^1H$ NMR. Partial $^1H$ NMR (400 MHz, $CDCl_3$) $\delta$ 4.41 (d, 1H, J=5.6 Hz, H-1 of $\beta$-anomer), 3.89 (d, 1H, J=3.2 Hz, H-1 of $\alpha$-anomer); Partial $^{13}C$ NMR (100 MHz, $CDCl_3$) $\delta$96.00 (C-1 of $\beta$-anomer), 90.31 (C-1 of $\alpha$-anomer).

4-Nitrophenyl (2,3,4,6-tetra-O-acetyl-$\alpha/\beta$-D-glucopyranosyl) Carbonate To a cooled solution (0° C.) of 2,3,4,6-tetra-O-acetyl-$\alpha/\beta$-D-glucopyranose (2a) (2.48 g, 7.13 mmol) in anhydrous $CH_2Cl_2$ (50 mL) were successively added 4-nitrophenyl chloroformate (1.72 g, 8.53 mmol) and triethylamine (2.96 mL, 21.3 mmol). After stirring for 4.5 hours at room temperature, the crude mixture was dilute with $CH_2Cl_2$ (50 mL) and then washed with brine and water. The organic solution was dried over anhydrous $Na_2SO_4$ then concentrated. After purification by silica gel column chromatography using EtOAc/hexane (½) as an eluent, 4-nitrophenyl (2,3,4,6-tetra-O-acetyl-$\alpha/\beta$-D-glucopyranosyl) carbonate (3.28 g, 6.39 mmol, yield 89.6%) was obtained as a 3:1 ($\alpha/\beta$) mixture of anomers as judged by $^1$H-NMR. The ratio may variate with reaction conditions changed. Partial $^1H$ NMR (500 MHz, $CDCl_3$) $\delta$ 6.28 (d, 1H, J=3.0 Hz, H-1 of $\alpha$-anomer), 5.66 (d, 1H, J=8.0 Hz, H-1 of $\beta$-anomer); Partial $^{13}C$ NMR (125 MHz, $CDCl_3$) $\delta$ 95.79 (C-1 of $\beta$-anomer), 94.05 (C-1 of $\alpha$-anomer). MS (ESI) m/z 536 $[M+Na]^+$, 1049 $[2M+Na]^+$.

1-(Cyanomethylamino) Morpholine

4-Aminomorpholine (2.04 g, 20.0 mmol) and formaldehyde-sodium bisulfite (2.68 g, 20.0 mmol) were dissolved in water (15 mL) and stirred at room temperature for 3 hours. To this reaction mixture was added KCN (1.3 g, 20.0 mmol) and the stirring was continued overnight at 60° C., then extracted with EtOAc (100 mL×2) and washed with brine. The extract was dried over anhydrous $Na_2SO_4$ and then concentrated to give 1-(cyanomethylamino) morpholine (1.4 g, 9.9 mmol, yield 49.5%) as a yellow oil. $^1$H NMR (500 MHz, CDCl$_3$) δ 4.26 (s, 1H, NH), 3.68 (t, 4H, J=5.0 Hz, H-6 & H-2), 3.65 (s, 2H, CH$_2$ of cyanomethylamino), 2.72 (s, 4H, H-5 & H-3); $^{13}$C NMR (CDCl$_3$, 125 MHz) δ 118.23 (CN), 66.67 (C-2 & C-6), 56.38 (C-5 & C-3) 37.48 (CH$_2$ of cyanomethylamino). MS (ESI) m/z 142 [M+H]$^+$. HRMS (EI) calc. for C$_6$H$_{11}$N$_3$O [M]$^+$141.09021 found 141.09023.

3-Morpholinosydnonimine Hydrochloride (SIN-1·HCl)

To a solution of 1-(cyanomethylamino) morpholine (1.4 g, 9.9 mmol) in water (20 mL) and conc. HCl (1.0 mL) was added dropwise a solution of NaNO$_2$ (821 mg, 11.9 mmol) in H$_2$O (5 mL). The reaction mixture was stirred for 15 minutes and then extracted with EtOAc (100 mL×2). The extract was dried over anhydrous Na$_2$SO$_4$ then concentrated to give a yellow oil, to which was added an excess amount of methanolic hydrochloric acid. The solution was stirred for 2 hours and concentrated to afford an off-white solid, which was collected by filtration and washed with ether. 3-Morpholinosydnonimine hydrochloride (1.40 g, 6.8 mmol, yield 68.7%) was obtained as a white crystal after recrystalization from ethanol. $^1$H NMR (500 MHz, DMSO-d$_6$) δ 9.64 (s, 2H, NH$_2$), 8.28 (s, 1H, H-4), 3.85 (t, 4H, J=5.0 Hz, H-6' & H-2'), 3.59 (t, 4H, H-5' & H-3'); $^{13}$C NMR (125 MHz, DMSO-d$_6$) δ 168.54 (C-5), 96.48 (C-4), 64.65 (C-2' & C-6'), 53.40 (C-5' & C-3'). MS (ESI) m/z 171[M−HCl+H]$^+$, 341 [2(M−HCl)+H]$^+$.

N-(2,3,4,6-Tetra-O-acetyl-α/β-D-glucopyranosyl)-carbonyl-3-morpholinosydnonimine To a solution of 4-nitrophenyl (2,3,4,6-tetra-O-acetyl-α/β-D-glucopyranosyl) carbonate (1.53 g, 2.98 mmol) in anhydrous pyridine (20 mL) was added 3-morpholinosydnonimine hydrochloride (678 mg, 3.28 mmol). The reaction mixture was stirred overnight and then the solvent was removed in vacuo to give a sticky oil. The residue was purified by silica gel column chromatography using EtOAc/CH$_2$Cl$_2$ (1/1) as an eluent. N-(2,3,4,6-Tetra-O-acetyl-α-D-glucopyranosyl)-carbonyl-3-morpholinosydnonimine (471 mg, 0.865 mmol, yield 29%) and N-(2,3,4, 6-tetra-O-acetyl-β-D-glucopyranosyl)-carbonyl-3-morpholinosydnonimine (164 mg, 0.301 mmol, yield 10%) were obtained and their configurations were determined by the coupling constants between H-1 and H-2. $^1$H NMR. β-form: $^1$H NMR (500 MHz, CDCl$_3$) δ 7.70 (s, 1H, H-4'), 5.72 (d, 1H, J=8.5 Hz, H-1), 5.26 (t, 1H, J=9.0 Hz, H-3), 5.20~5.10 (m, 2H, H-4 & H-2), 4.25 (dd, 1H, J=12.5, 4.0 Hz, H-6), 4.12 (dd, 1H, J=12.0, 2.0 Hz, H-6), 3.97 (t, 4H, J=5.0 Hz, H-2" & H-6"), 3.85 (dd, 1H, J=4.0, 2.0 Hz, H-5), 3.54 (t, 4H, J=5.0Hz, H-3" & H-5"), 2.06~1.98 (m, 12H, COCH$_3$×4); $^{13}$C NMR (125 MHz, CDCl$_3$) δ 174.26 (C-carbonate), 170.69 (C=O of Ac), 170.24 (C=O of Ac), 169.36 (C=O of Ac×2), 158.27 (C-5'), 99.82 (C-4'), 93.30 (C-1), 73.10 (C-3), 72.22 (C-5), 70.42 (C-2), 67.83 (C-4), 65.37 (C-2" & C-6"), 61.50 (C-6), 54.53 (C-3" & C-5"), 20.71 (CH$_3$ of Ac×2), 20.58 (CH$_3$ of Ac×2). MS (ESI) m/z 545 [M+H]$^+$, 567 [M+Na]$^+$, 1089 [2M+H]$^+$, 1111 [2M+Na]$^+$. α-form: $^1$H NMR (500 MHz, CDCl$_3$) δ 7.77 (s, 1H, H-4'), 6.31 (d, 1H, J=3.5 Hz, H-1), 5.63 (t, 1H, J=10.0 Hz, H-3), 5.15 (t, 1H, J=10.0 Hz, H-4), 5.06 (dd, 1H, J=10.0, 4.0 Hz, H-2), 4.28~4.26 (m, 2H, H-5 & H-6), 4.10~4.00 (m, 1H, H-6), 3.97 (t, 4H, J=5.0 Hz, H-2" & H-6"), 3.54 (t, 4H, J=5.0Hz, H-3" & H-5"), 2.10~1.97 (m, 12H, COCH$_3$×4); $^{13}$C NMR (125 MHz, CDCl$_3$) δ 174.73 (C-carbonate), 170.67 (C=O of Ac), 170.04 (C=O of Ac), 169.84 (C=O of Ac), 169.62 (C=O of Ac), 159.20 (C-5'), 99.69 (C-4'), 90.10 (C-1), 70.14 (C-3), 69.62 (C-2), 68.98 (C-5), 67.97 (C-4), 65.35 (C-2" & C-6"), 61.46 (C-6), 54.58 (C-3" & C-5"), 20.68 (CH$_3$ of Ac), 20.61 (CH$_3$ of Ac×2), 20.55 (CH$_3$ of Ac). MS (ESI) m/z 545 [M+H]$^+$, 567 [M+Na]$^+$, 1089 [2M+H]$^+$, 1111 [2M+Na]$^+$.

N-(β-D-glucopyranosyl)-carbonyl-3-morpholinosydnonimine

To a solution of N-(2,3,4,6-tetra-O-acetyl-β-D-glucopyranosyl)-carbonyl-3-morpholinosydnonimine (15 mg, 27.5 μmol) in anhydrous methanol (5 mL) was added NaOCH$_3$ to adjust the solution pH value to 8~9. The reaction mixture was stirred at room temperature for several hours and then strong acidic resin (Amberlyst @ 15 ion-exchange resin) was added to neutralize the reaction mixture. After removing the solvent in vacuo, the residue was purified by silica gel columnchromatography using CH$_2$Cl$_2$/CH$_3$OH (4/1) as an eluent. N-(β-D-Glucopyranosyl)-carbonyl-3-morpholinosydnonimine (10 mg, 26.6 μmol) was obtained as a colorless syrup in quantitative yield. $^1$H NMR (500 MHz, CD$_3$OD) δ 8.1 4 (s, 1H, H-4'), 5.39 (d, 1H, J=7.5 Hz, H-1), 3.95 (t, 4H, J=5.0 Hz, H-6" & H-2"), 3.83 (dd, 1H, J=11.5, 2.0 Hz, H-6), 3.66 (dd, 1H, J=12.0, 5.0 Hz, H-6), 3.62 (t, 4H, H-3" & H-5"), 3.40 (t, 1H, J=8.5 Hz, H-3), 3.38–3.32 (m, 2H, H-5 & H-4), 3.32~3.29 (m, 1H, H-2); $^{13}$C NMR (125 MHz, CD$_3$OD) δ101.37 (C-4'), 97.43 (C-1), 78.64 (CH), 78.00 (CH), 73.97 (CH), 71.20 (CH), 65.58 (C-2" & C-6"), 62.50 (C-6), 55.45 (C-3" & C-5"). MS (ESI) m/z 377 [M+H]$^+$, 399 [M+Na]$^+$, 753 [2M+H]$^+$, 775 [2M+Na]$^+$.

The references cited in this disclosure, except to the extent they may contradict any statements or definitions made herein, are hereby incorporated by reference in their entirety.

The foregoing disclosure includes the best mode devised by the inventors for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations. As such, the present invention should be limited only by the spirit and scope of the appended claims.

We claim:

1. A linsidomine (SIN-1) comprising a sugar moiety, a SIN-1 moiety and a glycosidic bond disposed between the sugar and SIN-1 moieties, said SIN-1 having the general structure wherein L is a bond or a bifunctional linker group and wherein R is the sugar moiety and comprises a carbohydrate.

2. The linsidomine compound SIN-1 according to claim 1, wherein L is a bifunctional linker group.

3. The linsidomine compound SIN-1 according to claim 2, wherein the linker group includes a carbonyl group.

4. The linsidomine compound SIN-1 according to claim 1, wherein R is a monosaccharide.

5. The linsidomine compound SIN-1 according to claim 4, wherein R is selected from the group consisting of glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, and tagatose.

6. The linsidomine compound SIN-1 according to claim 4, wherein R is glucose.

7. The linsidomine compound SIN-1 according to claim 4, wherein R is galactose.

8. The linsidomine compound SIN-1 according to claim 4, wherein A is a furanose or pyranose ring structure.

9. The linsidomine compound SIN-1 according to claim 1, wherein R is a disaccharide.

10. The linsidomine compound SIN-1 according to claim 9, wherein R is a member selected from the group consisting of sucrose, lactose, and maltose.

11. The linsidomine compound SIN-1 according to claim 1, wherein L Is a glycosidic bond.

12. The linsidomine compound SIN-1 according to claim 11, wherein the glycosidic bond is in an α configuration.

13. The linsidomine compound SIN-1 according to claim 11, wherein the glycosidic bond is in a β configuration.

14. A compound which is N-(β-D-glucopyranosyl)-carbonyl-3-morpholinosydnonimine, N-(α-glucopyranosyl)-carbonyl-3-morpholinosydnonimine, N-(β-D-galactopyranosyl)-carbonyl-3-morpholinosydnonimine, or N-(α-D-galactopyranosyl)-carbonyl-3-morpholinosydnonimine.

15. A pharmaceutical composition, comprising:
   a therapeutically effective amount of a linsidomine compound SIN-1, the linsidomine compound (SIN-1) comprising a sugar moiety, a SIN-1 moiety and a glycosidic bond between the sugar and SIN-1 moieties, the linsidomine compound SIN-1 having the general structure
   wherein L Is a bond or a bifunctional linker group and wherein R is the sugar moiety and comprises a carbohydrate; and
   a pharmaceutically acceptable carrier.

16. A pharmaceutical composition in accordance with claim 15, further comprising a therapeutically effective amount of a second linsidomine compound SIN-1, the second linsidomine compound (SIN-1) comprising a sugar moiety, a SIN-1 moiety and a glycosidic bond between the sugar and SIN-1 moieties, the second linsidomine compound SIN-1 having the general structure
wherein L is a bond or a bifunctional linker group and wherein R is the sugar moiety and comprises a carbohydrate.

17. A pharmaceutical composition according to claim 15, wherein the carrier comprises a liquid vehicle.

18. A pharmaceutical composition according to claim 17, wherein the liquid vehicle comprises a member selected from the group consisting of water, Ringers-Lactate. DMSO, ethanol, and glycerol.

19. A pharmaceutical composition according to claim 15, wherein the carrier comprises one or more pharmaceutically acceptable excipients.

20. A pharmaceutical composition according to claim 19, wherein said composition is in the form of a pill, tablet, lacquered tablet, coated tablet, hard gelatin capsule, soft gelatin capsule, solution, syrup, emulsion, suspension, aerosol, suppository, ointment, gel, or a paste.

* * * * *